United States Patent [19]

Dumas

[11] Patent Number: 4,810,690

[45] Date of Patent: Mar. 7, 1989

[54] NON-FLAMMABLE AIR FRESHENER COMPOSITION

[75] Inventor: Sylvie Dumas, Clermont Ferrand, France

[73] Assignee: Reckitt & Colman S.A., Massy Cedex, France

[21] Appl. No.: 170,098

[22] Filed: Mar. 10, 1988

Related U.S. Application Data

[63] Continuation of Ser. No. 74,980, Jul. 17, 1987, abandoned.

[30] Foreign Application Priority Data

Jul. 21, 1986 [FR] France .............................. 86 10555

[51] Int. Cl.$^4$ .............................................. A61K 7/46
[52] U.S. Cl. ........................................ 512/02; 556/19; 556/20
[58] Field of Search ...................... 512/2, 3, 1; 556/19, 556/20; 252/386

[56] References Cited

U.S. PATENT DOCUMENTS 4,137,196  1/1979  Sakurai et al. .................. 512/4
4,668,434  5/1987  Bowman ......................... 512/4

FOREIGN PATENT DOCUMENTS 2000683  10/1983  Australia .
0088727   2/1984   Japan ........................... 512/2
  25754   9/1984   Japan ........................... 512/4
1088727   4/1984   U.S.S.R. ....................... 512/4
1537613   1/1979   United Kingdom .

Primary Examiner—Werren B. Lone
Attorney, Agent, or Firm—Frederick H. Rabin

[57] ABSTRACT

A homogeneous liquid composition for use in air freshening devices comprising 3 to 15% of dimethyl methylphosphonate, 1 to 12% of fragrance, 40 to 65% of organic solvent and 15 to 50% of water (where percentages are percentage by weight of the total composition). The composition is non-flammable in use.

9 Claims, No Drawings

NON-FLAMMABLE AIR FRESHENER COMPOSITION

This is a continuation of application Ser. No. 74,980 filed on July 17, 1987, now abandoned.

This invention relates to compositions for use in air freshening devices to eliminate unpleasant smells and/or to produce a fragrant atmosphere, as for example in the environment of a room.

Various types of air freshening devices (air fresheners) are on the market; these either have a continuous action or not, and are based on very different types of diffusion technology and support technology, such as aerosols, gels, impregnated cellulose pads, electric evaporation, and liquid wick evaporators.

Liquid wick evaporators (that is, air fresheners comprising a liquid reservoir and a wick immersed therein, for transfer of the liquid to the surroundings via evaporation) are particularly effective for steady evaporation over a period of time. A further advantage is that it is easy to see when the air freshener composition has become exhausted.

The majority of such liquids are aqueous solutions (for economical reasons) which contain a small quantity of fragrance. In order to disperse fragrances in such solutions to give a homogeneous composition, surfactants have to be used: non-volatile surfactants tend to accumulate on the wick, thus inhibiting the rise of liquids up the wick, and eventually preventing evaporation altogether.

In order to ensure a long duration of action, a large amount of liquid is required, which in turn necessitates a large container. The consumer finds this unacceptable, on the grounds of aesthetic appearance and cost.

The potency of the air freshener will be increased if more fragrance is added: however, to maintain homogeneity, this will require the addition of increased amounts of surfactants, which may lead to premature blocking of the wick.

One solution to the problem is to use organic solvent-based formulae, which allow the dissolution of a larger quantity of fragrance. Consequently, only small amounts of surfactant, or no surfactant at all, are required, and overall volumes can be reduced without affecting the efficiency of the product. The solvent acts as the carrier for the fragrance. It helps the fragrance to rise up the wick and to evaporate on the surface.

Solvent formulations generally contain water for reasons of economy. However, this does not generally eliminate a potential drawback of such formulations, namely flammability.

It is possible however to construct the air freshener system in such a way that the evaporation surface can be isolated from any contact with flames. In general this necessitates a protective grating above the container: this can adversely affect evaporation performance. What is required is a compact air freshener system based on solvents which will give a satisfactory performance.

The applicant has discovered that using a particular co-solvent in a liquid will inhibit or totally suppress flammability of the vapours when the evaporant surface is in contact with flames. This eliminates the need to have a protective grating, giving a device which is cheaper to produce and more aesthetically appealing. Such a co-solvent is a phosphonate—in particular, dimethyl methylphosphonate (DMMP) which is a liquid previously employed for its flame-retardant properties in plastics and polyurethanes (see, for example, European patent publication No. 108713-A (Ciba-Geigy AG) and W German patent publication No. 27 40 589-A (Stauffer Chemical Co)).

We have now found that the incorporation of a small amount of DMMP into a homogeneous liquid air freshener composition with an organic solvent base can render the product non-flammable.

According to this invention, there is provided a non-flammable homogeneous air freshener composition comprising 3 to 15% dimethyl methylphosphonate, 1 to 12% of fragrance, 40 to 65% organic solvent and 15 to 50% water (where percentages are percentage by weight of the total composition).

In an aspect of the invention, the dimethyl methylphosphonate is in the range 4 to 8%, the fragrance 7 to 10%, the organic solvent 45 to 50% and the water is in the range 37 to 42%.

Suitable organic solvents are alcohols (for example, methanol, ethanol, 1-propanol and 2-propanol), glycols (for example, 1,2-ethanediol and 1,2-propanediol), mono- and diethers of glycols (for example, methyl and ethyl ethers of 1,2-ethanediol or 1,2-propanediol) and mixtures thereof. Clearly the amount of water present must be such that the fragrance and solvents are miscible therewith.

In another aspect of the invention, the composition comprises 4 to 8% dimethyl methylphosphonate, 7 to 10% fragrance, 45 to 50% 1,2-propanediol monoethyl ether and 37 to 42% water.

The amount of DMMP needed to make the composition non-flammable depends on the flammability of both the organic solvent and the fragrance, and on the proportions of organic solvent, fragrance and water present. Compositions with the ratio of the total weight of organic solvent plus fragrance to the weight of DMMP lying in the range 3:1 to 20:1 have been found to be particularly successful.

A further benefit of DMMP is that it is odourless, and does not therefore affect the deodorant properties of the solution.

It must be emphasised that it is not necessarily possible to ignite the air freshener composition directly, even without the incorporation of DMMP. The flammability problem arises when the composition is used in a liquid wick evaporator, in which small amounts of the composition are being delivered to the atmosphere. A useful analogy is that of the candle, in which the wax is not directly flammable, but is capable of sustaining a flame via a wick.

In order to demonstrate the non-flammability of a liquid/wick system, one can put 40 ml of the liquid into a 50 ml beaker with a diameter of ess that 46 mm. The evaporation mechanism, consisting of an evaporant surface (a disc of 50 mm diameter made of cotton or cellulose) and a wick (of cotton or cellulose), fastened in the middle, is placed on the beaker, with the wick dipping into the liquid. This is allowed to evaporate for 24 hours, after which time a lighted match is put on the evaporant surface. This is repeated three times. If there are no flames present when the match is withdrawn, the product can be described as being non-flammbale. If the vapours, however, burn after the match has been withdrawn, the product is deemed to be flammable.

The invention is illustrated by the Examples shown in the Table. The Table includes comparative Examples in which the DMMP has been omitted: Examples 1, 4, 7, 10, 12 (without DMMP) correspond to Examples 2, 5, 8, 11, 13 (with DMMP) in that the components are present in identical ratios to each other. Note that Examples 3, 6, and 9 are controls only, and not air freshener compositions.

| COMPOSITION | EXAMPLE | | | | | | | | | | | | |
|---|---|---|---|---|---|---|---|---|---|---|---|---|---|
| % w/w | 1 | 2 | 3 | 4 | 5 | 6 | 7 | 8 | 9 | 10 | 11 | 12 | 13 |
| Ethanol | 53.3 | 48 | — | — | — | — | — | — | — | — | — | — | — |
| 2-Methoxyethanol | — | — | 100 | 65.2 | 57.4 | — | — | — | — | — | — | — | — |
| 2-Ethoxyethanol | — | — | — | — | — | 100 | 60 | 57 | — | — | — | — | — |
| Napsol PE$_1$* | — | — | — | — | — | — | — | — | 100 | 47.4 | 45 | 52.6 | 50 |
| Water | 37.8 | 34 | — | 25.2 | 22.2 | — | 31.6 | 30 | — | 44.2 | 42 | 39.0 | 37 |
| Fragrance** | 8.9 | 8 | — | 9.6 | 8.4 | — | 8.4 | 8 | — | 8.4 | 8 | 8.4 | 8 |
| DMMP | — | 10 | — | — | 12 | — | — | 5 | — | — | 5 | — | 5 |
| Ratio - (solvent + fragrance): DMMP | | 5.6 | | | 5.5 | | | 13.0 | | | 10.6 | | 11.6 |
| Flammability | YES | NO | YES | YES | NO | YES | YES | NO | YES | YES | NO | YES | NO |

*1,2-Propanediol monoethyl ether
**Fragrances used: LF 11451 and 11453 (Bush Boake Allen)

From the Table, it can be seen that the addition of DMMP to an air freshener composition can be effective in eliminating the flammability of the composition.

Needless to say, this invention has been described purely for purposes of explanation and to no restrictive effect. The respective proportions of DMMP: fragrance: solvent: water can be varied without going outside its limits.

We claim:

1. A non-flammable homogeneous air freshener composition comprising 3 to 15% dimethyl methylphosphonate, 1 to 12% fragrance, 40 to 65% organic solvent and 15 to 50% water, where percentages are percentage by weight of the total composition.

2. A non-flammable homogeneous air freshener composition comprising 4 to 8% dimethyl methylphosphonate, 7 to 10% fragrance, 45 to 50% organic solvent, and 37 to 42% water, where percentages are percentage by weight of the total composition.

3. A composition as claimed in claim 1 in which the organic solvent comprises an alcohol, a glycol or a mono- or diether of a glycol, or mixtures thereof.

4. A composition as claimed in claim 1 in which the organic solvent comprises methanol, ethanol, 1-propanol, 2-propanol, 1,2-ethanediol, 1,2-propanediol, or a methyl, ethyl, dimethyl or diethyl ether of 1,2-ethanediol or 1,2-propanediol, or mixtures thereof.

5. A composition as claimed in claim 1 in which the organic solvent comprises ethanol, 2-methoxyethanol, 2-ethoxyethanol or 1,2-propanediol monoethyl ether, or mixtures thereof.

6. A composition as claimed in claim 2 in which the organic solvent comprises ethanol, 2-methoxyethanol, 2-ethoxyethanol or 1,2-propanediol monoethyl ether, or mixtures thereof.

7. A composition as claimed in claim 1, in which the ratio of the total weight of the organic solvent plus the weight of fragrance to the weight of dimethyl methylphosphate is in the range 3:1 to 20:1.

8. A method for suppressing the flammability of an air freshener composition comprising a fragrance and a flammable organic solvent, which method comprises adding to the air freshener composition from about 3 to about 15 weight %, based on the total weight of the composition, of dimethyl methylphosphonate.

9. A method according to claim 8 in which 2 to 8 weight % of dimethyl methylphosphonate is added.

* * * * *